US00PP10190P

United States Patent [19]

Zaiger et al.

[11] Patent Number: Plant 10,190

[45] Date of Patent: Jan. 13, 1998

[54] PEACH TREE 'SNOW JEWEL'

[76] Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave., all of Modesto, Calif. 95358

[21] Appl. No.: 731,280

[22] Filed: Oct. 11, 1996

[51] Int. Cl.[6] ..... A01H 5/00

[52] U.S. Cl. ..... Plt./42.1

[58] Field of Search ..... Plt./42.1

*Primary Examiner*—James R. Feyrer

[57] ABSTRACT

A new and distinct variety of peach, *Prunus persica*, tree with the following unique combination of desirable features:

1. Heavy and regular production of large, white flesh, clingstone fruit.
2. Fruit with a mild, sweet, subacid flavor with excellent eating quality.
3. Fruit with firm white flesh, good handling and shipping qualities.
4. An attractive fruit with a white ground color nearly overspread with a red blush.
5. Large tree size with vigorous, upright growth.
6. Relatively uniform ripening of fruit throughout the tree.

1 Drawing Sheet

ORIGIN OF THE VARIETY

The present new variety of peach tree was developed in our experimental orchard located near Modesto, California, as a first generation cross between a selected seedling (field identification number 20GA1054) and White Lady Peach (U.S. Plant Pat. No. 5,821). The maternal parent (20GA1054) originated from a cross of Rhone Gold Nectarine (non-patented) with Redwing Peach (U.S. Plant Pat. No. 621). We planted and grew a large number of these first generation seedlings under close observation and the present variety exhibited the distinct and desirable fruit characteristics described above and was selected for asexual reproduction and commercialization.

ASEXUAL REPRODUCTION OF THE VARIETY

The present variety of peach tree was asexually propagated by budding, as performed in our experimental orchard located near Modesto, Calif., and shows that all characteristics of the tree and its fruit run true to form and are established and transmitted through succeeding asexual propagations.

SUMMARY OF THE VARIETY

A new and distinct variety of peach tree which is of large size, vigorous, upright growth, and a regular and productive bearer of large, white flesh, clingstone fruit with excellent flavor and eating quality. The fruit is further characterized by having firm flesh with good handling and shipping quality, being relatively uniform in ripening throughout the tree, having a high degree of attractive red skin blush and, in comparison to the White Lady Peach (U.S. Plant Pat. No. 5,821), the new variety is approximately 18 days earlier in maturity.

PHOTOGRAPH OF THE VARIETY

The accompanying photographic illustration shows typical specimens of the foliage and fruit of the new variety. The upper and lower surface of the leaves are shown, along with an exterior and sectional view of the fruit divided in the suture plane showing flesh coloration, pit cavity and stone remaining in place. The photographic illustration was taken shortly after being picked at maturity (firm ripe) and the colors are as nearly true as is reasonably possible in a color representation of this type.

DESCRIPTION OF THE VARIETY

The following is a detailed botanical description of the new and distinct variety of peach tree, its flowers, foliage and fruit, as based on observations of the variety grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Productivity.*—Productive.
- *Bearer.*—Regular.
- *Density.*—Medium dense.

Trunk:
- *Size.*—Medium stocky.
- *Texture.*—Medium shaggy.
- *Color.*—Brown to soot brown (5-E-5) to (5-F-5).

Branches:
- *Size.*—Medium.
- *Texture.*—Smooth to medium rough, varies with age of growth.
- *Lenticels.*—Numerous. Small in size.
- *Color.*—Reddish brown to brown (5-D-7) to (5-E-6). Varies with age of growth.

Leaves:
- *Size.*—Large. Average length 6". Average width 1½".
- *Form.*—Lanceolate, pointed.
- *Margin.*—Crenate.
- *Thickness.*—Medium.
- *Surface.*—Smooth.
- *Petiole.*—Medium length. Medium thickness.
- *Glands.*—Number varies from 1 to 5. Average number 2. Medium to large size. Reniform. Located on upper portion of petiole and lower portion of leaf blade.
- *Color.*—Upper surface — green to dark green (29-F-6) to (29-F-8). Lower surface — light green to green (29-E-6) to (29-E-8).

Flower buds:
- *Size.*—Large.
- *Length.*—Medium.

*Form.*—Plump.
*Pubescence.*—Pubescent.

Flowers:
*Size.*—Large, showy.
*Pollen.*—Present, self-fertile.
*Blooming period.*—Date of first bloom: Mar. 3, 1994. Date of full bloom: Mar. 7, 1994. Varies slightly with climatic conditions.
*Color.*—Pink.

Fruit:
*Maturity when described.*—Firm ripe.
*Date of first picking.*—Jun. 22, 1994.
*Date of last picking.*—Jun. 26, 1994.
*Size.*—Large. Average diameter axially 2⅞" to 3". Average transversely in suture plane 2⅞" to 3".
*Form.*—Nearly globose, some fruit slightly compressed in suture plane.
*Suture.*—Shallow, nearly rounded, extends from base to apex.
*Ventral surface.*—Usually rounded, varies from rounded to slightly lipped.
*Apex.*—Varies from slight pistil point to rounded.
*Base.*—Retuse.
*Cavity.*—Rounded, slightly elongated in suture plane.

Flesh:
*Ripens.*—Evenly.
*Texture.*—Firm.
*Fibers.*—Few, small, tender.
*Aroma.*—Moderate.
*Amygdalin.*—Undetected.
*Eating quality.*—Excellent.
*Flavor.*—Excellent, mild, sweet, subacid.
*Color.*—White to pinkish white (6-A1) to (6-A-2). Pit cavity, pinkish white to grayish white (6-A-2) to (6-B-2). Very slight bleeding of grayish white color into flesh from pit cavity.

Skin:
*Thickness.*—Medium.
*Texture.*—Medium, tenacious to flesh.
*Down.*—Moderate, medium length.
*Tendency to crack.*—None.
*Color.*—White to pinkish white ground color (7-A-1) to (7-A-2). Nearly overspread with red to orient red (10-C-6) to (10-C-8).

Stone:
*Type.*—Clingstone.
*Size.*—Medium to large. Average length 1⅜". Average breadth 1 1/16". Average thickness ⅝".
*Form.*—Obovate.
*Base.*—Usually straight, varies from straight to rounded.
*Apex.*—Cuspidate.
*Surface.*—Irregularly furrowed toward apex, pitted toward base. Pit cavities vary from round to elongated. Ridges unusually rounded.
*Sides.*—Equal to unequal.
*Tendency to spilt.*—None.
*Color.*—Light brown to reddish brown (10-C-6) to (10-D-7).

Use: Dessert.
*Market.*—Local and long distance.

Keeping quality: Good.

Shipping quality: Good.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous, upright growth and being a productive and regular bearer of large white flesh fruit with excellent flavor and eating quality; the fruit is further characterized by having a high degree of attractive red skin color, having firm flesh with good handling and shipping quality and, in comparison to White Lady Peach (U.S. Plant Pat. No. 5,821), the new variety is aproximately 18 days earlier in maturity.

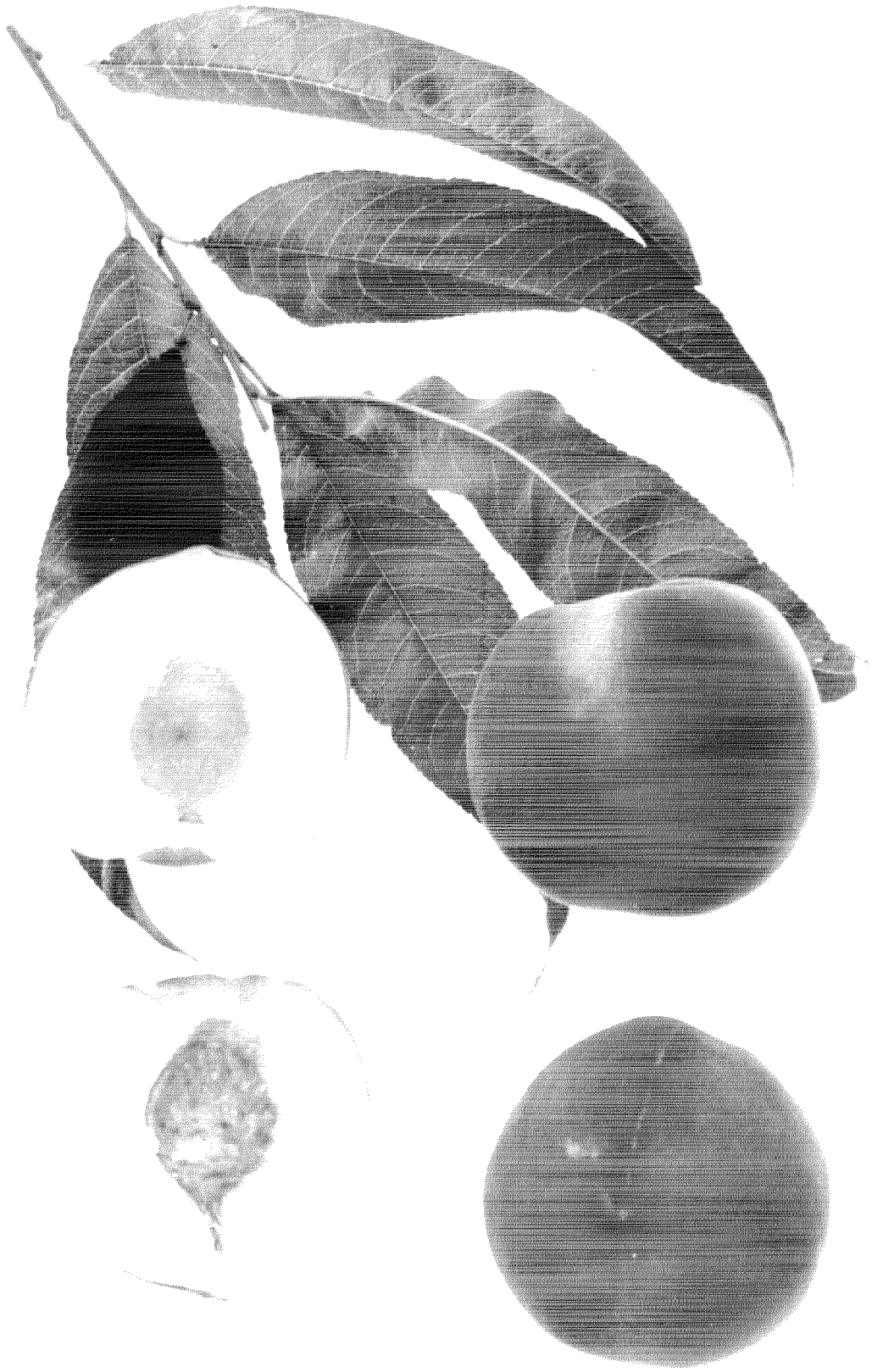

* * * * *